(12) United States Patent
Buchberger (10) Patent No.: US 11,484,670 B2
(45) Date of Patent: *Nov. 1, 2022

(54) LAMINAR EVAPORATOR (71) Applicant: BATMARK LIMITED, London (GB)

(72) Inventor: Helmut Buchberger, Ennsdorf (AT)

(73) Assignee: NICOVENTURES TRADING LIMITED, London (GB)

(*) Notice: Subject to any disclaimer, the term of this patent is extended or adjusted under 35 U.S.C. 154(b) by 377 days.

This patent is subject to a terminal disclaimer.

(21) Appl. No.: 16/594,480

(22) Filed: Oct. 7, 2019

(65) Prior Publication Data

US 2020/0046915 A1 Feb. 13, 2020

Related U.S. Application Data (63) Continuation of application No. 15/398,981, filed on Jan. 5, 2017, now Pat. No. 10,449,308, which is a
(Continued)

(30) Foreign Application Priority Data

Mar. 10, 2010 (AT) ...................................... 386/2010

(51) Int. Cl.
*A61M 11/04* (2006.01)
*A24F 40/44* (2020.01)
(Continued)

(52) U.S. Cl.
CPC ............ *A61M 11/042* (2014.02); *A24F 40/44* (2020.01); *A24F 40/46* (2020.01); *A61M 11/041* (2013.01);
(Continued)

(58) Field of Classification Search
CPC .. A61M 11/00; A61M 11/041; A61M 11/042; A61M 11/044; A61M 15/00;
(Continued)

(56) References Cited

U.S. PATENT DOCUMENTS 4,223,292 A 9/1980 Morikawa et al.
4,588,976 A 5/1986 Jaselli
(Continued)

FOREIGN PATENT DOCUMENTS

CN 201375023 Y 1/2010
EP 2110033 A1 10/2009
(Continued)

OTHER PUBLICATIONS

Application and File History for U.S. Appl. No. 14/927,556, filed Oct. 30, 2015, inventors Blandino et al.
(Continued)

Primary Examiner — Joseph D. Boecker
(74) Attorney, Agent, or Firm — Patterson Thuente Pedersen, P.A.

(57) ABSTRACT

The disclosure relates to a laminar evaporator including an electrical resistance heating element for pulse heating and evaporation of an inhalationally receivable material distributed or distributable on the heating element surface by an electric heating current flowing or flowable in a laminar manner with at least two electrical contacts or poles for introducing the heating current into the resistance heating element, wherein the resistance heating element has at least one slot-shaped recess constricting lines of flux of an original electric field forming or formable between the at least two electrical contacts or poles and comprises a porous structure having a porosity of 70% or greater holding or capable of holding the material.

12 Claims, 8 Drawing Sheets

Related U.S. Application Data continuation of application No. 13/583,381, filed as application No. PCT/AT2011/000123 on Mar. 10, 2011, now Pat. No. 9,555,199.

(51) Int. Cl.
- *A24F 40/46* (2020.01)
- *A61M 15/00* (2006.01)
- *A24F 40/10* (2020.01)

(52) U.S. Cl.
CPC .............. *A61M 15/00* (2013.01); *A24F 40/10* (2020.01); *A61M 2205/3653* (2013.01); *H05B 2203/021* (2013.01)

(58) Field of Classification Search
CPC ............ A61M 2205/3653; A24F 47/00; A24F 47/004; A24F 47/008; H05B 2203/021
See application file for complete search history.

(56) References Cited

U.S. PATENT DOCUMENTS

| | | | |
|---|---|---|---|
| 4,735,217 A | 4/1988 | Gerth et al. | |
| 4,922,901 A | 5/1990 | Brooks et al. | |
| 5,060,671 A * | 10/1991 | Counts .................... | A24F 40/30 131/329 |
| 5,095,921 A | 3/1992 | Losee et al. | |
| 5,179,966 A | 1/1993 | Losee et al. | |
| 5,222,362 A | 6/1993 | Maus et al. | |
| 5,322,075 A | 6/1994 | Deevi et al. | |
| 5,530,225 A | 6/1996 | Hajaligol | |
| 5,613,505 A | 3/1997 | Campbell et al. | |
| 5,666,978 A | 9/1997 | Counts et al. | |
| 5,692,525 A | 12/1997 | Counts et al. | |
| 5,771,845 A | 6/1998 | Pistien et al. | |
| 6,124,579 A | 9/2000 | Steinhauser et al. | |
| 6,155,268 A | 12/2000 | Takeuchi | |
| 6,671,450 B2 | 12/2003 | Khan et al. | |
| 7,374,063 B2 | 5/2008 | Reid | |
| 8,156,944 B2 | 4/2012 | Han | |
| 8,948,578 B2 | 2/2015 | Buchberger | |
| 10,449,308 B2 * | 10/2019 | Buchberger .......... | A61M 15/00 |
| 2002/0113685 A1 | 8/2002 | Izaki et al. | |
| 2003/0049025 A1 * | 3/2003 | Neumann ................ | A61L 9/03 392/390 |
| 2003/0186474 A1 | 10/2003 | Haluzak et al. | |
| 2004/0096204 A1 | 5/2004 | Gerhardinger | |
| 2004/0247302 A1 | 12/2004 | Toya et al. | |
| 2005/0063686 A1 | 3/2005 | Whittle et al. | |
| 2005/0211711 A1 | 9/2005 | Reid | |
| 2005/0268911 A1 | 12/2005 | Cross et al. | |
| 2007/0074734 A1 | 4/2007 | Braunshteyn et al. | |
| 2007/0155255 A1 | 7/2007 | Galauner et al. | |
| 2008/0047956 A1 | 2/2008 | Dudman | |
| 2008/0216828 A1 | 9/2008 | Wensley et al. | |
| 2009/0126745 A1 | 5/2009 | Hon | |
| 2009/0220222 A1 | 9/2009 | Rabin et al. | |
| 2009/0272379 A1 | 11/2009 | Thorens et al. | |
| 2011/0155153 A1 | 6/2011 | Thorens et al. | |
| 2011/0226236 A1 | 9/2011 | Buchberger | |
| 2013/0081623 A1 * | 4/2013 | Buchberger .......... | A61M 11/042 128/203.27 |
| 2014/0182608 A1 | 7/2014 | Egoyants et al. | |
| 2015/0030317 A1 | 1/2015 | Bayer et al. | |
| 2015/0040925 A1 | 2/2015 | Saleem et al. | |
| 2015/0059780 A1 | 3/2015 | Davis et al. | |

FOREIGN PATENT DOCUMENTS

| | | |
|---|---|---|
| EP | 2316286 A1 | 5/2011 |
| JP | H03277265 A | 12/1991 |
| JP | H1189551 A | 4/1999 |
| JP | 2004298331 A | 10/2004 |
| JP | 2005511178 A | 4/2005 |
| JP | 2009537120 A | 10/2009 |
| WO | WO-0167819 A1 | 9/2001 |
| WO | WO-03037412 A2 | 5/2003 |
| WO | WO-03049535 A1 | 6/2003 |
| WO | WO-03103387 A2 | 12/2003 |
| WO | WO-2010045671 A1 | 4/2010 |
| WO | WO-2011079932 A1 | 7/2011 |

OTHER PUBLICATIONS

Application and File History for U.S. Appl. No. 14/382,198, filed Aug. 29, 2014, inventors Saleem et al.

Davies, et al., "Metallic Foams: Their Production, Properties and Applications," Journal of Materials Science, 1983, vol. 18(7), pp. 1899-1911.

International Preliminary Report on Patentability for Application No. PCT/AT2011/000123, dated Sep. 20, 2012, 6 pages.

International Search Report and Written Opinion for Application No. PCT/EP2013/057539, dated Feb. 11, 2014, 16 pages.

International Search Report and Written Opinion for Application No. PCT/AT2011/000123, dated Jul. 18, 2011, 8 pages.

Office Action dated Sep. 29, 2015 for Japanese Application No. 2015-506185 filed Apr. 11, 2013, 5 pages.

Search Report dated Oct. 15, 2014 for Japanese Application No. 2012-556343, 18 pages.

Warrier M., et al., "Effect of the Porous Structure of Graphite on Atomic Hydrogen Diffusion and Inventory," Nucl. Fusion, vol. 47, 2007, pp. 1656-1663.

\* cited by examiner

LAMINAR EVAPORATOR

CROSS REFERENCE TO RELATED APPLICATIONS

This application is a continuation of application Ser. No. 15/398,981 filed Jan. 5, 2017, which in turn is a continuation of application Ser. No. 13/583,381 filed Dec. 17, 2012, now U.S. Pat. No. 9,555,199, issued Jan. 31, 2017, which in turn is a 35 U.S.C. § 371 National Phase conversion of PCT/AT2011/000123, Mar. 10, 2011, which claims benefit of Austrian Patent Application No. A 386/2010, filed Mar. 10, 2010, each of which is hereby fully incorporated herein by reference. The PCT International Application was published in the German language.

TECHNICAL FIELD

The disclosure relates to a laminar flow evaporator.

BACKGROUND

Definition of Terms

The term "inhalationally receivable material" covers in principle any material inhalable by a human being and/or a user. The evaporated material can be supplied to the user in the form of a vapor-air mixture and/or a condensation aerosol. The material may contain a drug, or consist of a drug preparation; in addition, it may contain only components which are not defined as drugs.

"Pulse heating and evaporation" is present if the material is heated and evaporated within the time interval of an inhalation, thus within a few seconds or within fractions of a second.

The "electrical heating current which flows or can flow in a laminar manner through the resistance heating element" can be a direct current or an alternating current.

Known laminar evaporators, as described, for example, in U.S. Pat. No. 4,735,217 (Donald L. Gerth et al.), US 2005/0268911 (Steven D. Cross et al.), U.S. Pat. No. 5,060,671 (Mary E. Counts et al.), U.S. Pat. No. 5,095,921 (D. Bruce Losee et al.) and U.S. Pat. No. 4,922,901, FIG. 4-8 (Johnny L. Brooks et al.), exhibit to a large extent constant temperature conditions over large regions of evaporation surface—cf., for example, US 2005/0268911, FIGS. 17a and 17b. Greater temperature gradients occur in any case in the region of the electrical contacts, where the electric current is introduced into the laminar resistance heating element, and heat flows parasitically into adjacent structural components. Otherwise, however, the temperature distribution is very even. This even temperature distribution can also be a disadvantage, particularly if the material to be evaporated contains components with different boiling points. The laminar constant temperature distribution has the effect in this case that the material with the lower boiling point evaporates first in the course of the pulse energy input and the material with the higher boiling point only begins to evaporate if the lower boiling material has already to a large extent evaporated and has already left the vaporization zone. This effect is unfavorable if the two materials immediately after their evaporation and/or release are intended to interact with one another in a certain way, in order to give rise, for example, to certain pharmacological and/or pharmacokinetic effects, or to favor such effects. An example of such interaction is the accumulation of an otherwise volatile material on an aerosol-forming substance. Aerosol-forming substances are characterized by particularly low vapor pressures. Glycerol (glycerine) may be cited as one example of an aerosol-forming substance. Aerosol-forming substances have the task of actually binding otherwise volatile materials and in this way to improve their accessibility to the lungs in order, for example, to enable supply of a systemically active substance. A further example of such an interaction is the protonation of nicotine by acids and/or the formation of appropriate nicotine salts. Nicotine essentially evaporates as a free base. Free nicotine in base form is, however, readily volatile and in this form hardly accessible to the lungs. The majority of the nicotine base would already have been separated at an earlier stage. A systemic nicotine administration via the lung alveoli can hardly be effected in this way. If nicotine recombines with an acid immediately after its evaporation and/or release, however, its volatility can be substantially reduced, in particular even if aerosol-forming substances are available at the same time. In a glowing cigarette these conditions are fulfilled during a puff in an optimal way. This is to be attributed above all to the steep temperature gradient between the glow zone and the evaporation and distillation zone. The temperature falls here from over 8000 to below 1000 within a few millimeters. Under these conditions aerosol-forming substances, organic acids and nicotine are set free practically simultaneously in the narrowest area, even if the boiling points and/or release temperatures of the aerosol-forming substances and organic acids differ substantially from the boiling point of nicotine (246° C.). Consequently, there is a high probability that under these conditions nicotine will recombine with an acid and be deposited on already condensed aerosol particles. With filterless cigarettes these conditions lead in the long run to the majority of the nicotine transferred into the main stream smoke actually reaching the lung alveoli so that the desired systemic effect can unfold in the central nervous system within seconds.

SUMMARY

It is the task of the disclosure to remedy the above-indicated disadvantages of the known arrangements of laminar evaporators of the state of the art. In particular, it is the task of the disclosure to design a laminar evaporator of the type described above in such a way that as steep a temperature decrease and/or as large a temperature gradient as possible in the surface direction and in the narrowest area is produced in the evaporating material during the pulse current supply, so that the individual substances contained in the material are released as synchronously as possible.

The task is solved in that the resistance heating element has at least one slot-shaped recess constricting the lines of flux of the original electric field forming or formable between the poles and/or is connected superficially with an open-celled porous structure which holds or can hold the material.

Definition of terms: The "original electric field" is any electric field which would be formed in the resistance heating element, if no slot-shaped recess in accordance with the invention were present.

The open-celled porous structure can be formed, for example, from a fabric, an open-pored fibrous structure, an open-pored sintered structure, an open-pored foam or an open-pored deposition structure. A combination of these structures is also possible. Furthermore the structures can be laminated one above the other in several layers.

On analogy with a flowing watercourse, the slot-shaped recess works like a bar extending across the water flow:

zones with an increased and zones with a decreased current flow both form in the region around the slot-shaped recess. The fact that the electric power density is proportional to the square of the current density leads to the heat introduced into the resistance heating element fluctuating greatly from one point to another within the region around the slot-shaped recess and steep temperature gradients are formed in the surface direction. The temperature gradient can be realized in the closest area, i.e. within distances which correspond to the expansion of the slot-shaped recess. The heat introduced is transferred by thermal conduction to the material stored in the immediately adjacent porous structure. Here two characteristics of the porous structure which are relevant to the present disclosure become involved: on the one hand the characteristic that the heat conductivity in porous structures decreases disproportionately with increasing porosity; on the other hand the characteristic that porous structures can also take up and fix comparatively large amounts of material. The porous structure thus works against both a heat exchange and an exchange of material in the surface direction. These characteristics have the effect that the temperature gradients formed in the resistance heating element are hardly affected by the porous structure and the same temperature gradients can also form to a comparable extent in the porous structure and in the long run in the material to be evaporated. Finally, it can also be considered advantageous that the calorific losses of the resistance heating element as a whole are not increased by the slot-shaped recess.

In a further advantageous embodiment of the disclosure it is provided that the porous structure consists of an electrically resistant material and the slot-shaped recess also intersperses the porous structure. The porous structure thus even becomes a part of the resistance heating element. This arrangement has the advantageous effect that the heat is produced at least partly directly in the porous structure and is transferred there directly to the material to be evaporated. As previously mentioned, the heat conductivity in porous structures decreases disproportionately with increasing porosity. Although this characteristic proves advantageous with regard to the formation of temperature gradients in the surface direction, this characteristic is to be considered as disadvantageous if it also leads to a temperature gradient in the thickness direction. A temperature gradient in the thickness direction can severely disrupt evaporation and thus the efficiency of the evaporator inasmuch as this favors the occurrence of a boiling crisis. This is valid particularly in those cases where the porous structure is completely or to a large extent saturated with the material to be evaporated. Because the heat is, at least in part, produced directly in the porous structure, the formation of a temperature gradient in the thickness direction can be effectively combated. In a special case in accordance with the invention the resistance heating element can be formed entirely of the porous structure. The heat is produced in this case completely in the porous structure. Such arrangements naturally make it possible to achieve the highest evaporating capacity, particularly if the pores of the porous structure are exposed on both sides, i.e. communicate freely with the environment, and vapor can therefore leak out of the laminar heating element on both sides. The pores of the porous structure are not considered to be recesses in the sense of the present application, even if they are slot-shaped. A slot-shaped recess is considered as being in accordance with the invention only if it extends over at least several pores.

It is particularly advantageous if the slot-shaped recess runs essentially in a straight line and is aligned at least approximately at right angles to the constricted lines of flux of the original electric field. To evaluate whether or not the above-specified conditions are met, any unimpaired lines of flux of the original electric field which are most strongly constricted by the slot-shaped recess should be evaluated geometrically. It can be shown that slot-shaped recesses of a given size have the largest pinch effect if they meet the above-mentioned geometrical conditions.

In accordance with one embodiment of the disclosure, the slot-shaped recess consists of a cut. The cut is preferably made by means of laser cutting procedures. A laser cutting procedure allows the production of particularly fine slots. Thus by using the laser precision cutting procedure, for example by means of an Nd:YAG laser, precision slots and/or cuts with a width of about 50 µm can be produced. Such fine cuts make it possible to constrict the lines of flux of the electrical source field, without demanding a substantial surface for it, so that—from a geometrical point of view—almost the entire original heating element surface remains available for the evaporation.

In a further advantageous embodiment of the disclosure, the resistance heating element and the porous structure consist of a high-resistivity metallic material. The laser cutting of laminar metallic materials such as sheet metals, metal foils and metal fabrics is today routinely accomplished. Thus making a cut in such materials in accordance with the invention does not represent a large technological challenge, even if the material exhibits a porous structure. Suitable metallic high-resistivity materials are, for example: high-grade steels such as AISI 304 or AISI 316 as well as heat-conducting alloys—in particular NiCr alloys and CrFeAl alloys ("Kanthal") such as DIN material numbers 2.4658, 2.4867, 2.4869, 2.4872, 1.4843, 1.4860, 1.4725, 1.4765 and 1.4767. The invention is, however, by no means limited to these metals and/or alloys. The afore-mentioned metals have a comparatively high electrical conductivity compared with many non-metallic high-resistivity materials. Accordingly high heating currents are the result. Particularly if these currents have to be obtained from batteries, one is perhaps technologically already up against certain boundaries. In this connection the slot-shaped cut in accordance with the invention proves advantageous inasmuch as the resistance of the heating element is increased by the cut. In addition, the slot makes it possible to attain an accurate adjustment of a given target resistance value.

In a further extension of the disclosure, several or a plurality of slot-shaped recesses are provided. By providing several or a plurality of slot-shaped recesses, several and/or a plurality of zones with locally distinct temperature gradients can be created on the heating element surface and the advantageous effects already described become effective over a wide area.

In accordance with the disclosure the slot-shaped recesses can be unevenly closely distributed on the heating element surface. By distributing the slot-shaped recesses unevenly a second type of temperature gradient is superimposed on the resistance heating element and/or the porous structure, which overlies the zones with locally distinct temperature gradients and is thus effective over a wider area. More generally formulated, the uneven distribution of the slot-shaped recesses can influence the current and power density distribution. Thus, for example, zones with high current density can be relieved by introducing slot-shaped recesses, since the flow will now go around these zones.

In a particularly advantageous further development of the laminar evaporator in accordance with the disclosure, it is provided that the porous structure forms a wick. The capillary action of the wick causes the porous structure to refill automatically in this case with liquid material after pulse evaporation. For this purpose the porous structure only needs to be brought into contact with a source of liquid. The porous structure thus works multi-functionally in this embodiment.

In addition, the disclosure relates to an inhaler component, comprising a laminar evaporator in accordance with the disclosure, as described above, as well as a source of liquid, communicating and/or capable of communicating via capillary with the wick to supply the wick with the liquid substance. It is intended in accordance with the disclosure that the wick is supplied with the liquid substance in the direction of the lines of flux of the original electric field and the slot-shaped recesses are arranged one behind the other graduated in a row aligned essentially parallel to the lines of flux. The filling of the wick with the liquid substance towards the lines of flux of the original electric field can be more advantageously effected via an electrical contact base so that additional calorific losses can be avoided. By the grouping of the slot-shaped recesses in rows a zone reserved for the wick is produced which, to a large extent, is free of slot-shaped recesses and via which the porous structure can be supplied with the liquid substance to a large extent unhindered. The slot-shaped recesses can also be graduated in several rows.

As an alternative to the variant arrangement just described, it can also be provided in accordance with the disclosure that the wick is supplied with the liquid substance transverse to the lines of flux of the original electric field, and the slot-shaped recesses are essentially in the direction of filling. This arrangement has the advantage that the slot-shaped recesses obstruct the capillary liquid flow least, but requires, beside the electrical contacts, a further base for the capillary contact of the wick.

BRIEF DESCRIPTION OF THE DRAWINGS

Appropriate and advantageous examples of the disclosure are represented in the drawings and are described below in more detail. The drawings show.

DETAILED DESCRIPTION

Table 1 shows the material specifications of an exemplary laminar evaporator in accordance with the disclosure.

According to this the laminar evaporator consists of six layers: a metal foil and five metal wire meshes sintered onto it. The metal in the present example consists of the heat-conducting alloy NiCr8020, DIN material number 2.4869. Different heat-conducting alloys could of course also be used. Heat-conducting alloys can be ordered as starting material from the company ThyssenKrupp VDM GmbH, www.thyssenkruppvdm.de, and then processed into foils, fine wires and wire meshes. ThyssenKrupp VDM GmbH supplies the previously mentioned material NiCr8020, DIN material number 2.4869, under the trade name "Cronix 80", which can also be fused to a very pure specification with a carbon content<0.02%. The company Record Metall-Folien GmbH, www.recordmetall.de, in co-operation with its suppliers, is in a position to make available metal foils from a thickness of 5 µm from starting material preferably in the form of strip. The company J. G. Dahmen & Co. GmbH & Co. KG, www.dahmen-draht.de, is able to draw fine wires starting from a thickness of 18 µm from starting material that can be in the form of wire. The fine wires can subsequently be routinely woven into wire mesh by wire weaving mills, for example by the companies Haver & Boecker, www.haverboecker.com, or Sporl KG, www.spoerl.de.

The metal foil and the wire mesh layers are connected by sintering. Sintering can take place under vacuum or under a protective atmosphere of hydrogen. Such sintering counts as state of the art and can be routinely carried out, for example, by the company GKN Sinter Metals Filters GmbH, www.gkn-filters.com, as well as by the company Sporl KG, www.spoerl.de. Sintering is advantageously effected in the form of multiple cutouts; that is, the individual laminar evaporators are not sintered, but larger area cutouts are used, for example in the format 200×200 mm. The individual laminar evaporators are obtained from the multiple cutouts after sintering by laser cutting or stamping machines.

Instead of heat-conducting alloys, stainless steels, e.g. AISI 304L or AISI 316L, are also used as alternative materials for the laminar evaporator in accordance with the invention. These have substantial cost advantages over NiCr8020, but nevertheless have a distinctly lower electrical resistance compared with NiCr8020. To increase the electrical resistance the stainless steel laminar evaporators or the intermediate products of which they are made—the multiple cutouts—can optionally be etched.

Material is evenly removed by etching. The etching can advantageously be carried out in an aqueous pickling bath consisting of 50% nitric acid and 13% hydrofluoric acid. Such pickling baths can be supplied under the designation "Avesta 302" by the company Avesta Finishing Chemicals, www.avestafinishing.com. A favorable side effect of the etching is that it also increases the porosity of the laminar evaporator somewhat, as a result of which the evaporator becomes more absorptive for the material to be evaporated. However, the additional process of etching at least partly reduces the original cost advantages compared with heat-conducting alloys.

An interesting option also consists of combining heat-conducting alloys and stainless steels, where the more substantial layers can consist of a heat-conducting alloy and the finer layers of stainless steel. In the specific example in accordance with Table 1, this option could mean, for example, that the three outside layers, namely layers 3 to 5, could be made of stainless steel.

TABLE 1

Material specifications

| Material: | NiCr8020 | DIN 2.4869, "Cronix80" |
|---|---|---|
| Metal foil thickness | 5 μm | alternatively 10 μm |
| 1st wire mesh layer: | 90 × 36 μm | mesh size × wire size |
| 2nd wire mesh layer: | 71 × 30 μm | mesh size × wire size |
| 3rd wire mesh layer: | 56 × 20 μm | mesh size × wire size |
| 4th wire mesh layer: | 65 × 20 μm | mesh size × wire size |
| 5th wire mesh layer: | 45 × 18 μm | mesh size × wire size |
| Thickness: | 222 μm | after sintering |
| Porosity: | 70% | |
| Specific electrical resistance: | 8.4 [mOhm mm] | |
| Heat conductivity: | 2.1–2.7 *) [W/mK] | |

*) in the temperature range 20° C. to 400° C.

With laminar evaporators constructed in accordance with Table 1 the porous structure is formed by sintering the wire mesh layers with one another. Both the wire mesh layers and the metal foil make a contribution to the resulting electrical resistance heater. The values for specific electrical resistance and for the heat conductivity stated in Table 1 are of course valid in the surface direction. The values decrease disproportionately as the porosity increases.

Figure 1:
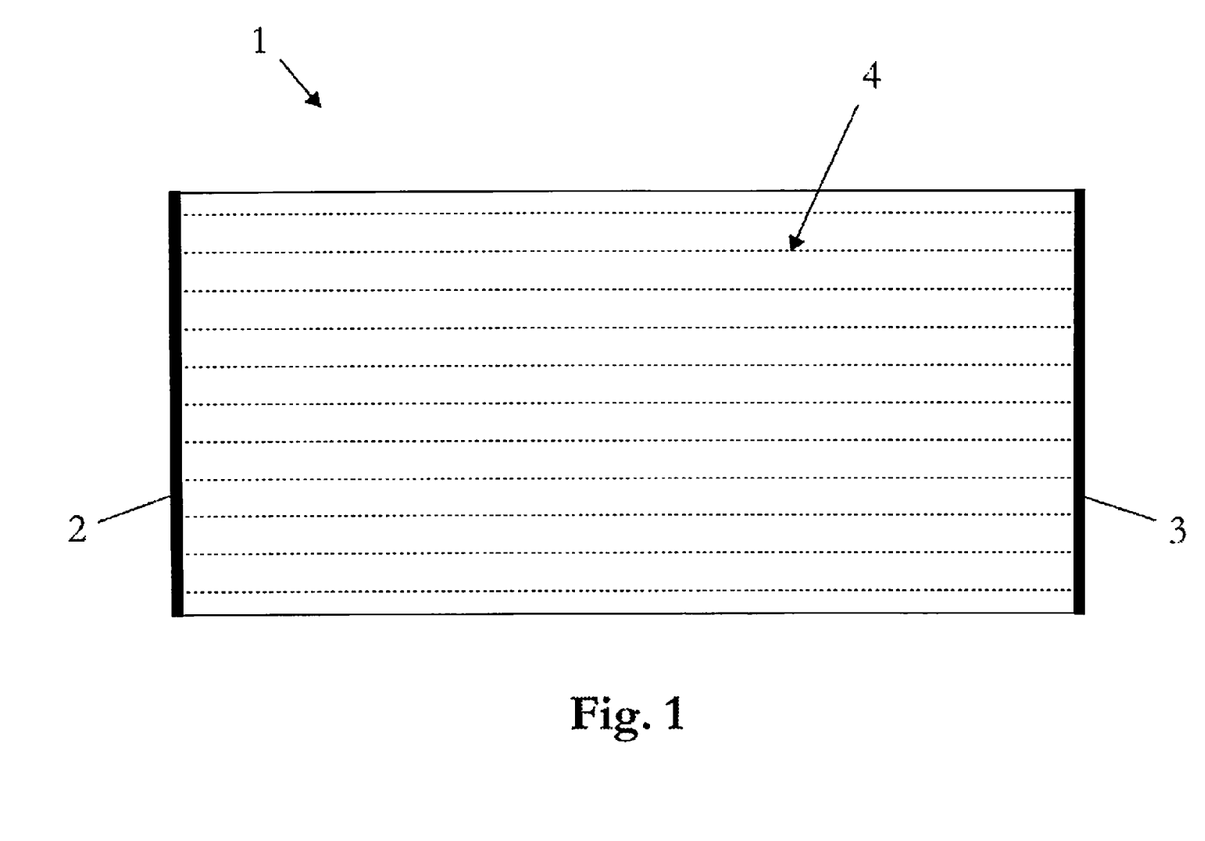
FIG. 1 a laminar evaporator without slot-shaped recesses.

FIG. 1 shows an example of a rectangular arrangement of a laminar evaporator 1. The dimensions of the evaporator amount to: length=12 mm, width=5.6 mm. The structure of the evaporator corresponds to that of Table 1. The evaporator and/or its electrical resistance material is electrically contacted at its narrow ends, thus forming two poles 2, 3 at these ends, over which the heating current is fed in and out. The heating current flows as soon as a voltage is applied to the poles 2, 3. The arrangement shown in FIG. 1 can also represent only a heated or heatable cutout of a laminar evaporator 1. The resistance material, including the porous structure, can continue outside via the poles 2, 3. For example, the laminar evaporator 1 can be contacted beyond the poles 2, 3, such as on the foil side, by means of an electrically conducting adhesive or by a welded joint, which at the same time also effects a mechanical attachment of the evaporator. The linear poles 2, 3 would in this case represent the outside boundary of laminar contact. As can be easily checked, the resulting heat resistance of the laminar evaporator shown in FIG. 1 amounts to 81 mOhm. FIG. 1 furthermore shows the lines of flux 4 of the original electric field forming between the poles 2, 3, if a voltage is applied to the poles 2, 3. Consequently, the lines of flux run in a straight line and connect the two poles in the shortest way. The evaporator arrangement shows an absolutely homogeneous current and power density distribution.

Figure 2:
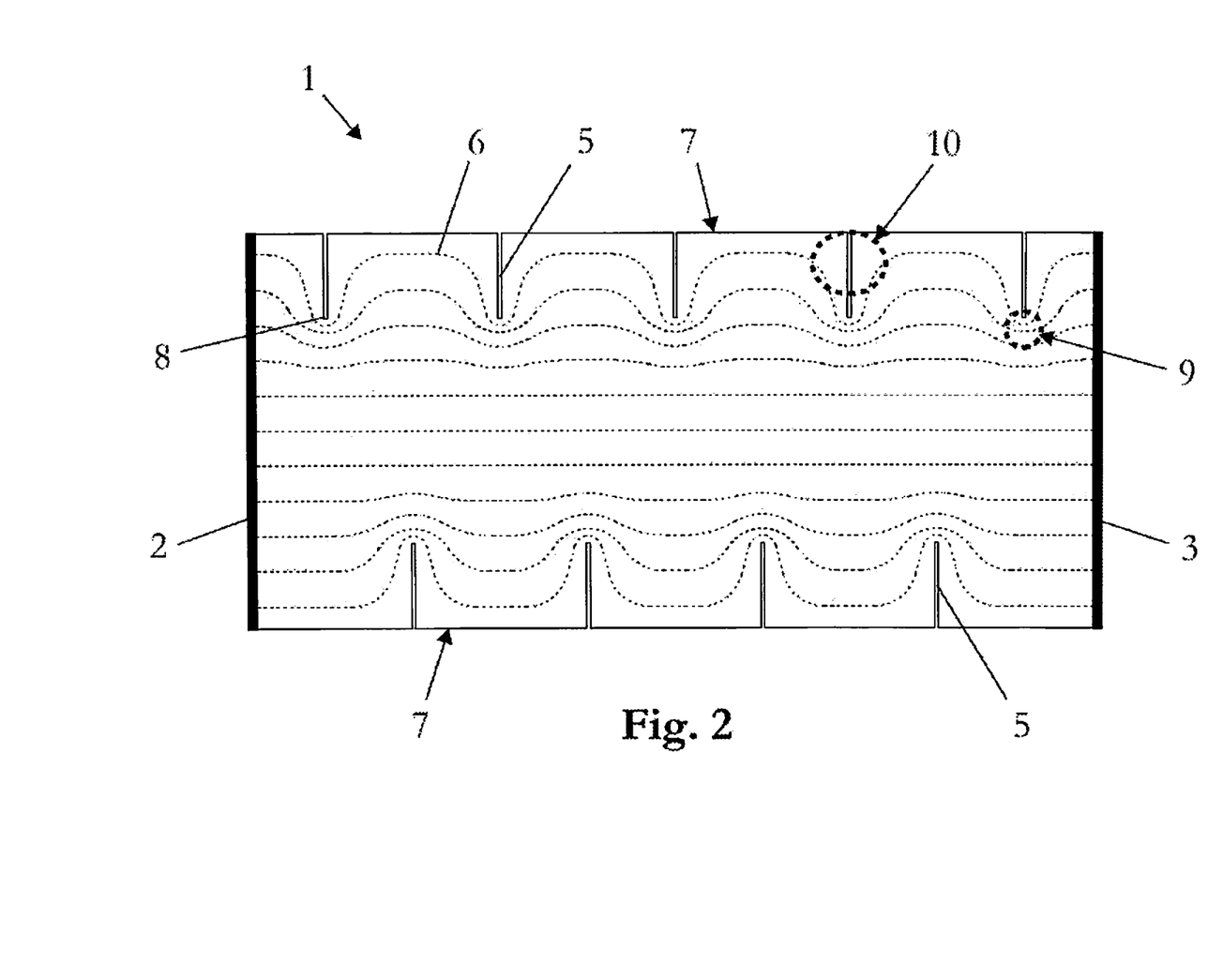
FIG. 2 a laminar evaporator in accordance with the invention with slot-shaped recesses.

FIG. 2 shows the same laminar evaporator as FIG. 1, but now with slot-shaped recesses 5 in accordance with the invention. The recesses 5 are aligned at right angles to the lines of flux 4 of the original electric field (see FIG. 1), as a result of which these lines of flux are constricted. The constricted lines of flux are marked in FIG. 2 by the reference symbol 6. Altogether nine slots 5 are provided. The slots are formed as cuts in the specific example. The length of the cuts is 1.2 mm. The cuts 5 proceed from opposite edges 7 of the laminar evaporator 1. The cuts can advantageously be made by means of an Nd:YAG laser. With this cutting procedure, cuts with a width of 50 μm, for instance, can be made. The advantages of such fine cuts have already been shown earlier. By the cuts 5 the resulting heating resistance of the laminar evaporator rises to 110 mOhm, i.e. an increase of approximately 35%.

Figure 3:
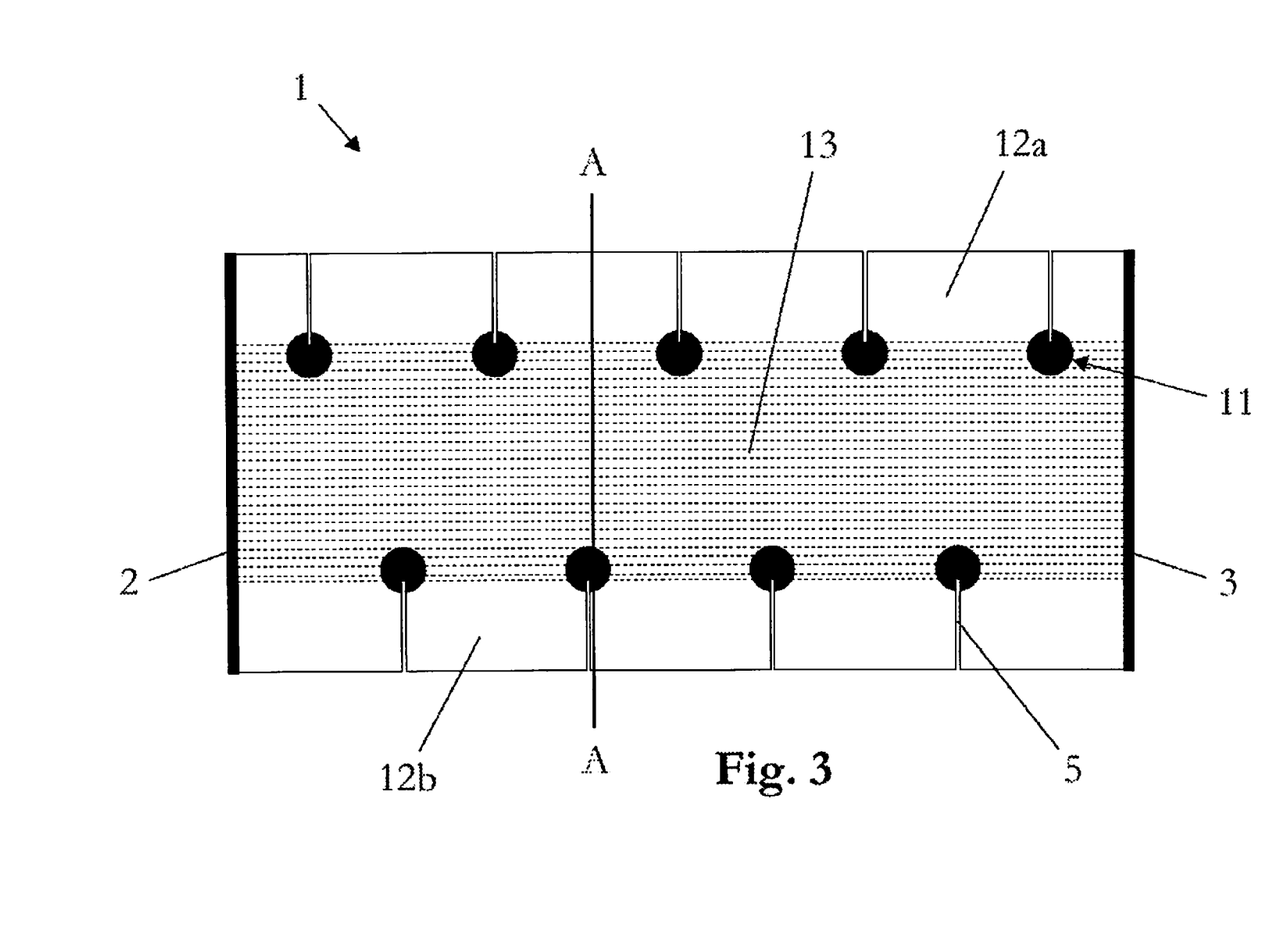
FIG. 3 the power density distribution of the laminar evaporator in accordance with FIG. 2.

The constriction of the electrical lines of flux 6 entails an uneven distribution of the electric field strength. Specifically, in zone 9 directly bordering the ends of 8 of the cutouts 5, where the lines of flux are most strongly constricted, particularly high field strengths arise almost selectively, while in the zones 10 bordering the cuts 5 the field strength exhibits comparatively low values. Since the field strength enters the calculation of the electric power density as a square, it can be expected that the electric power density will vary even more, which FIG. 3 shows to be the case. In broad terms, three zones can be differentiated: on the one hand immediately adjacent to the ends of the cuts 5 and again almost selectively zones 11 of the highest power density (shown in black); on the other hand, two border zones 12a and 12b of the lowest power density extending over the long sides of the laminar evaporator 1, which extend in the width direction approximately up to the ends of the cuts 5 (shown in white); and finally a central zone 13 of medium power density, which essentially extends between the edge zones 12a and 12b (shown dotted). This markedly non-homogeneous power density distribution together with the poor heat conductivity of the porous structure also results in the formation of steep temperature gradients during the pulse heating in the porous structure and concomitantly in the material to be evaporated. The following arithmetical example and the results from it are based on the evaluation of the heat conductivity equation for the geometry shown in FIG. 2 and on the conditions in accordance with Tables 2 and 3.

Table 2 describes the composition of the material to be evaporated. Accordingly, the material in the specific example consists of a nicotine solution highly diluted with ethanol and water. Glycerol is used as an aerosol former. Furthermore a range of organic acids are added to protonate the nicotine. The pores of the porous structure are completely filled with the nicotine solution, as a result of which a total of 10.4 μL nicotine solution is stored in the porous structure. The material released in the course of the evaporation is essentially determined by the ternary system ethanol-water-glycerol. The task of releasing the ingredients set out in Table 2 as synchronously as possible will succeed if the two groups of main materials, the solvent (ethanol and water) on the one hand and the aerosol former (glycerol) on the other hand, are released as synchronously as possible. The fact that this task is not simple can be seen from the substantially different material properties of these groups of materials alone—see Table 2a.

TABLE 2

Example of drug preparation based on nicotine

| Material | CAS number | % by weight |
|---|---|---|
| Ethanol | 64-17-5 | 67.13 |
| Water | 7732-18-5 | 17.72 |
| Glycerol | 56-81-5 | 11.08 |
| Nicotine | 54-11-5 | 1.33 |
| Lactic acid | 50-21-5 | 0.11 |
| Succinic acid | 110-15-6 | 0.18 |
| Levulinic acid | 123-76-2 | 0.40 |
| Benzoic acid | 65-85-0 | 0.07 |
| Acetic acid | 64-19-7 | 1.30 |
| Formic acid | 64-18-6 | 0.43 |
| Solanon | 1937-54-8 | 0.07 |
| Tobacco flavouring oils | | 0.18 |
| Total: | | 100.00 |

TABLE 2a

Material properties ethanol-water-glycerol

| | Boiling point | Vapour pressure at 20° C. |
|---|---|---|
| Ethanol | 78° C. | 5800 Pa |
| Water | 100° C. | 2340 Pa |
| Glycerol | 290° C. | <0.1 Pa |

In solving the heat conduction equation the electric power density shown in FIG. 3 is entered as the heat source. To calculate the power density a DC voltage of 1.5 V applied to the poles 2, 3 was taken as a basis, where the current is supplied with a variable duty cycle in accordance with Table 3. In this way the energy input can be controlled as desired throughout the pulse heating and evaporation. The resulting useful voltage is thus a square wave signal of constant amplitude but with a variable pulse duty factor. Furthermore, the temperature was constant at the poles 2, 3 at an ambient temperature (20° c.), which broadly also applies if the laminar evaporator 1 is at the same time also attached to the poles.

TABLE 3

Current flow - modulation percentage [%]

| Time [s] | [%] |
|---|---|
| 0.00-0.52 | 100 |
| 0.52-0.55 | 80 |
| 0.55-0.60 | 60 |
| 0.60-0.70 | 40 |
| 0.70-1.40 | 35 |
| 1.40-1.50 | 25 |
| 1.50-1.55 | 15 |
| 1.55-1.60 | 10 |
| 1.60-2.00 | 0 |

Figure 4:
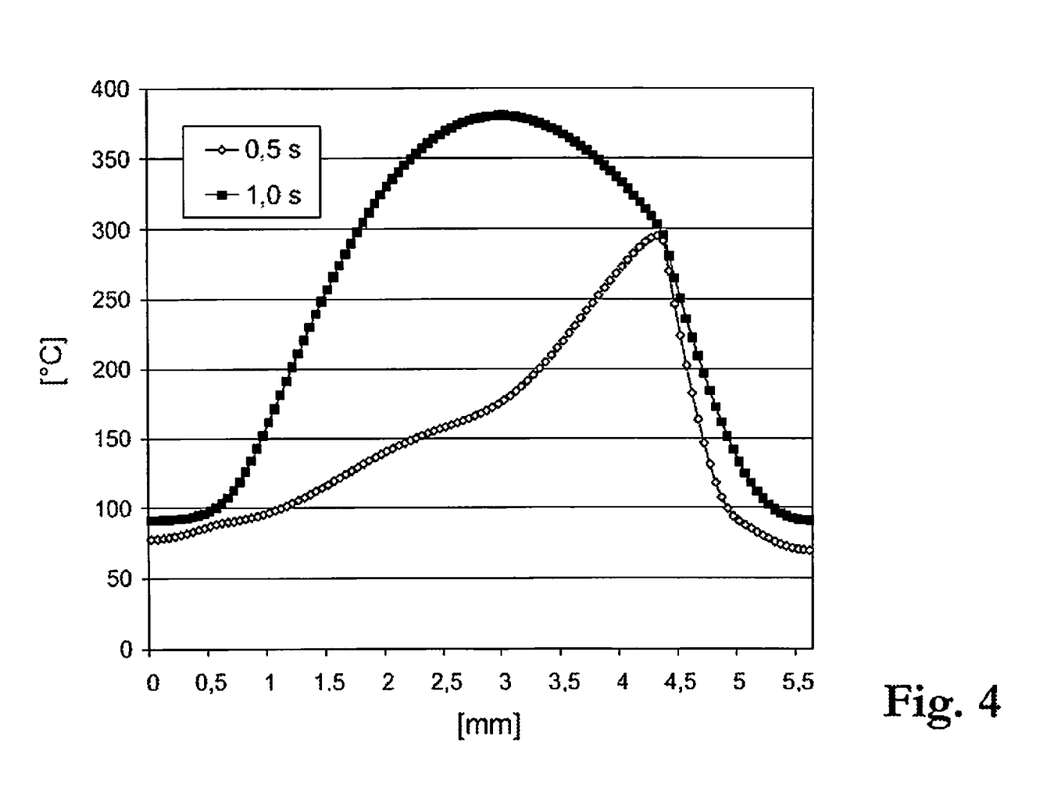
FIG. 4 the temperature distribution in the cross section A-A in accordance with FIG. 3 during pulse heating and evaporation.

FIG. 4 shows as a first result of the evaluation the temperature distribution in the cross section A-A in accordance with FIG. 3, 0.5 and/or 1.0 seconds after the start of pulse heating. According to this, temperature gradients in the order of magnitude of 200° C./mm, and even up to 350° C./mm in some cases, occur in the porous structure and hence also in the nicotine solution. These values are already quite near enough to the temperature gradients arising in a glowing cigarette.

Figure 5:
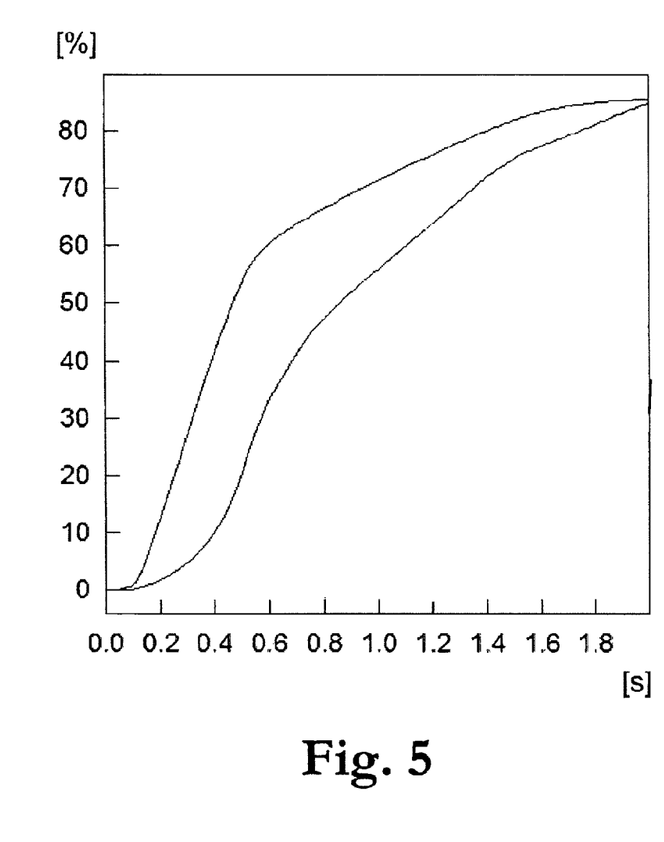
FIG. 5 the material release of the laminar evaporator in accordance with FIG. 2 during pulse evaporation.
Figure 6:
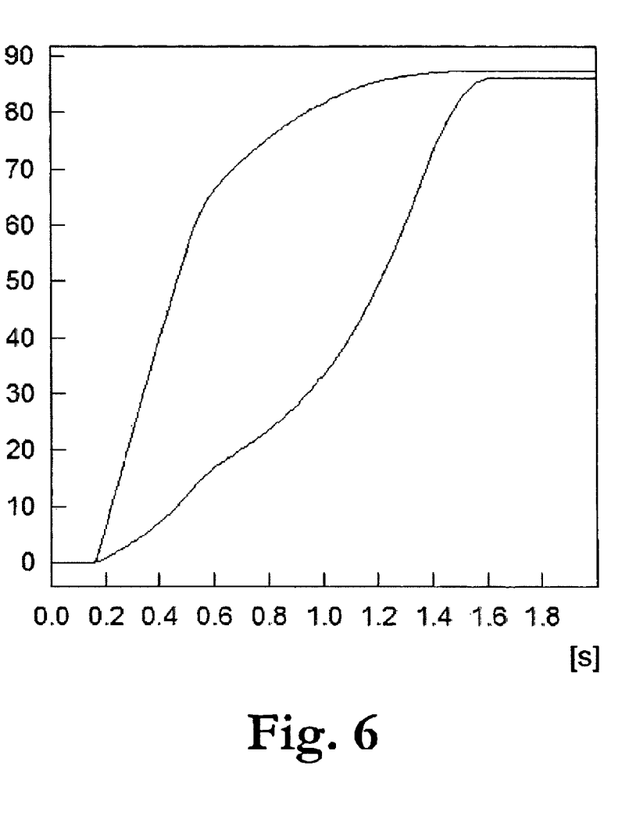
FIG. 6 the material release of the laminar evaporator in accordance with FIG. 1 during pulse evaporation.

FIG. 5 shows as a further result of the simulation the quantities of solvents (ethanol and water) and aerosol former (glycerol) released cumulatively during pulse evaporation. The values are proportional and refer to the starting quantities originally stored in the porous structure. In the calculation it was assumed that the release of the individual components of the ternary system ethanol-water-glycerol is only temperature-dependent and that this dependence can to a close approximation be recorded by an exponential law. The upper curve represents the solvent, the lower curve the aerosol former. FIG. 6, in direct comparison to this, shows the material release on using a laminar evaporator, as shown in FIG. 1, hence without any slots, where the voltage applied to the poles 2, 3 was reduced to 1.3 V (same power density) because of the now lower heating resistance. It is possible to see immediately how substantial is the influence of the slot-shaped recesses and/or cuts 5 on the dynamics of the release. The material release in accordance with FIG. 5 runs extremely synchronously while the solvent and the aerosol former in the example in accordance with FIG. 6 are released in almost the opposite direction. From this it may be concluded that the slit laminar evaporator 1 in accordance with FIG. 2 appears substantially better suited for supplying a systemically active substance via the lung alveoli, in the specific example of a systemic nicotine administration, than an evaporator without such slots.

The slot length must be adjusted to the specific material properties of the laminar evaporator, in particular to the heat conductivity of the porous structure, where in the long run a compromise must be found: excessively long slots and/or cuts lead to zones being formed locally with no or very little evaporation. The material to be evaporated is only slightly heated in such zones. Such zones can also be called dead zones, because they play little or no part in the evaporation. If the slot length is made too short, however, the potential of the slot to form steep temperature gradients will not be exploited to the fullest extent.

The supply of the laminar evaporator 1 with electric current in accordance with FIG. 2 can be by means of a rechargeable battery. In the current state of the art, lithium ion as well as lithium polymer cells in particular are offered for this purpose. These cell types at present offer the highest power densities and flows and have been widely used for a long time, where mention should be made particularly of their widespread use in mobile phones. If two laminar evaporators 1 in accordance with FIG. 2 are electrically connected in series and the energy supply is effected on the basis of an individual lithium polymer cell with a nominal or an open circuit voltage of 3.7 V and a working voltage under a load of approximately 3 V, then the current which flows through the laminar evaporators is calculated as 13.6 A on the basis of Ohm's law. This amperage can be drawn from today's lithium polymer cells without any problem. Cell type SLPB533459H4 from the manufacturer Kokam Co., Ltd., www.kokam.com, can be cited as an example. The dimensions of the cell are: 58.5.times.33.5.times.5 mm (L×B×H) with a weight of 19.5 g. The cell has a capacity of 740 mAh and is able to supply a continuous current of 14.8 A. If one takes a pulse current flow according to Table 3 as a basis, then the two evaporators, connected in series, draw a quantity of electricity of around 4.4 mAh per pulse evaporation. Therefore up to 168 evaporation cycles and/or inhalations would theoretically be possible with the above-mentioned Kokam cell. This value may well not be fully achieved because of the relatively high amperage and the pulsed nature of the current requirements. The cell mentioned can, however, be recharged very quickly.

FIGS. 7A and 7B show an evaporator arrangement within an inhaler component, where the laminar evaporator 1 is identical in geometry and structure to the arrangement in accordance with FIG. 2. The laminar evaporator 1 is connected preferably on the foil side to two end sections on two electrically conducting plate-shaped contact elements 14*a* and 14*b*, with the surface of which it is also at the same time in electrical contact. Contact can take place, for example, via a laminar adhesive joint by means of a conductive adhesive, e.g. from the company Epoxy Technology, www.epotek-.com. The filament current flows as soon as a voltage is applied to the contact elements 14*a* and 14*b*. Since the electrical conductivity of the contact elements 14*a* and 14*b* is many times greater than the conductivity of the laminar evaporator 1, the outside boundaries 15*a* and 15*b* of the contact elements, that is those places in which the laminar evaporator 1 first touches the contact elements 14*a* and 14*b*, can be understood as poles 2, 3. The pole 2 is suggested in FIG. 7A by a thick line. The laminar evaporator 1 extends with an end section into a capillary gap 16. The capillary gap 16 is formed by the contact element 14*b* and an upper section 17 disposed on this superficially, by forming a corresponding recess, e.g. a milled slot, in the upper section 17. The capillary gap 16 communicates with a liquid reservoir 18 (shown symbolically in FIG. 7). The liquid reservoir 18 contains the material to be evaporated and/or the liquid to be evaporated 19. The liquid 19 could consist, for example, of a diluted drug preparation; such a preparation has, for example, already been described in Table 2. Furthermore, a ventilation hole 20 is provided in the contact element 14b, which likewise communicates with the liquid reservoir 18. The arrangement has the following effect: the capillary gap 16 draws liquid from the liquid reservoir 18 as a result of the capillary forces working in it, so that the capillary gap 16 fills with liquid 19. The liquid 19 comes into contact with the porous structure of the laminar evaporator 1 in the capillary gap 16. The porous structure is moistened by the liquid 19 and for its part acts like a wick, so that the entire porous structure of the laminar evaporator 1 fills automatically with the liquid 19. To balance the quantity of the liquid taken, air flows from the environment through the ventilation hole 20 into the liquid reservoir 18. After every pulse heating and evaporation of the liquid 19 the filling procedure is repeated. The porous structure in this case acts multi-functionally: first of all the porous structure supports the formation of steep temperature gradients in the liquid 19 to be evaporated because of its low heat conductivity; secondly it holds the liquid 19 in its pores during the evaporation, so that an exchange of material in the surface direction is prevented and temperature gradients already formed are not disturbed; and thirdly after pulse evaporation it automatically refills with the liquid to be evaporated 19 as a result of the capillary forces acting in it.

Figure 7A:
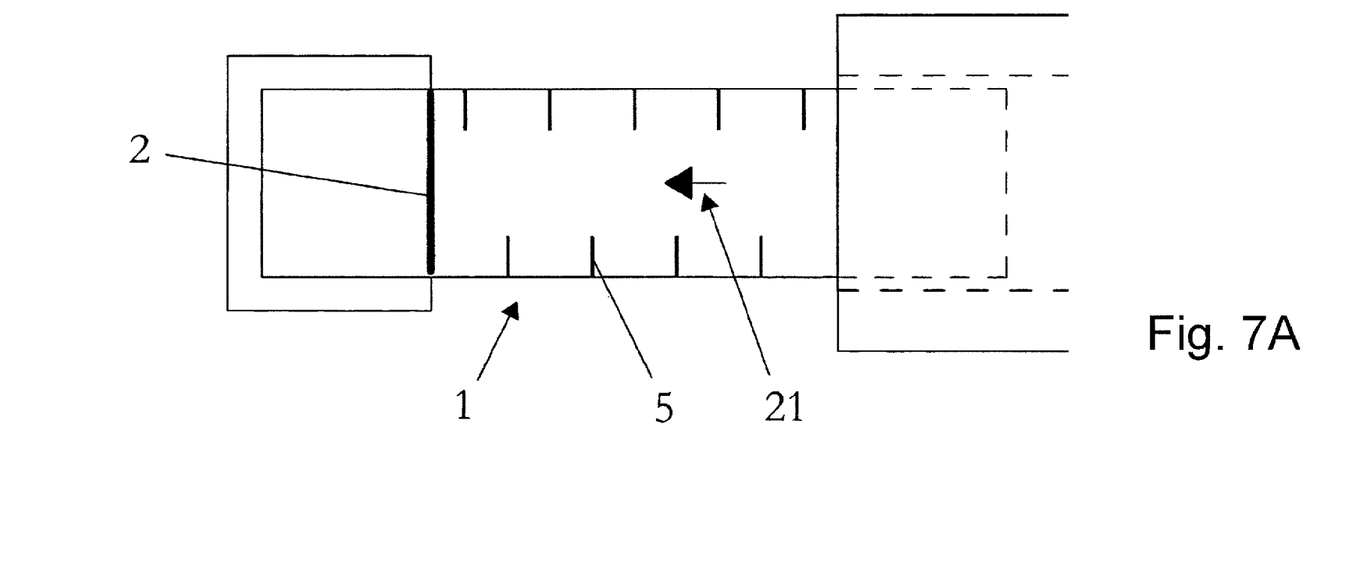
FIG. 7A is a top plan view of an evaporator arrangement with automatic liquid supply.
Figure 7B:
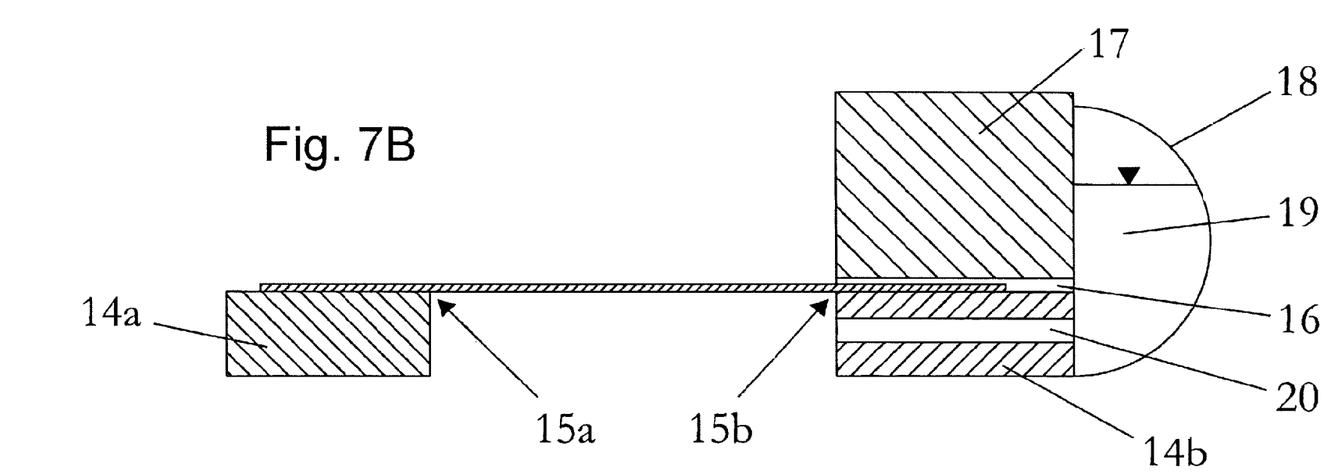
FIG. 7B is a sectional view of the evaporator arrangement of FIG. 7A.

The supply of the capillary structure with the liquid 19 to be evaporated takes place in the example in accordance with FIG. 7A in the direction of the lines of flux 4 of the original electric field (see FIG. 1). The slot-shaped recesses and/or cuts 5 are arranged staggered one behind the other aligned in two rows substantially parallel to the lines of flux. This creates a central main supply vein 21 reserved for the wick, which is to a large extent free from slot-shaped recesses and over which the porous structure can be supplied with the liquid 19 to a large extent unhindered (suggested in FIG. 7A by an arrow).

Figure 8:
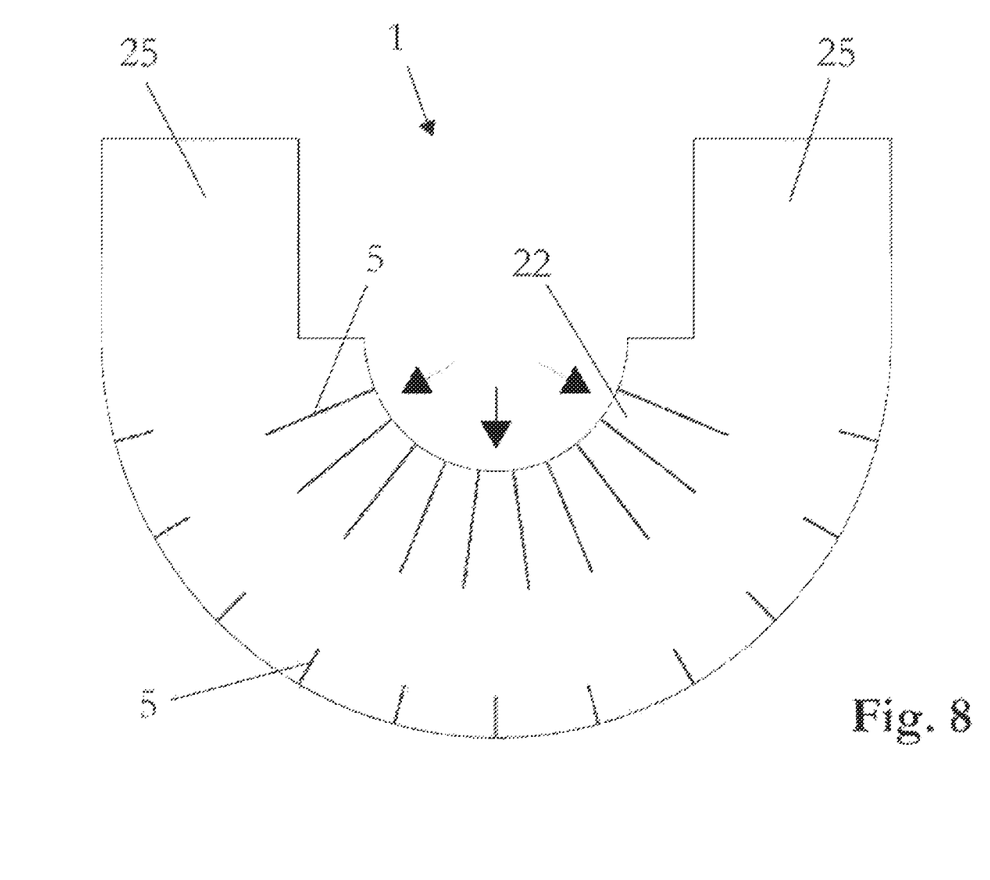
FIG. 8 is a further evaporator arrangement with automatic liquid supply.
Figures 9A, 9B:
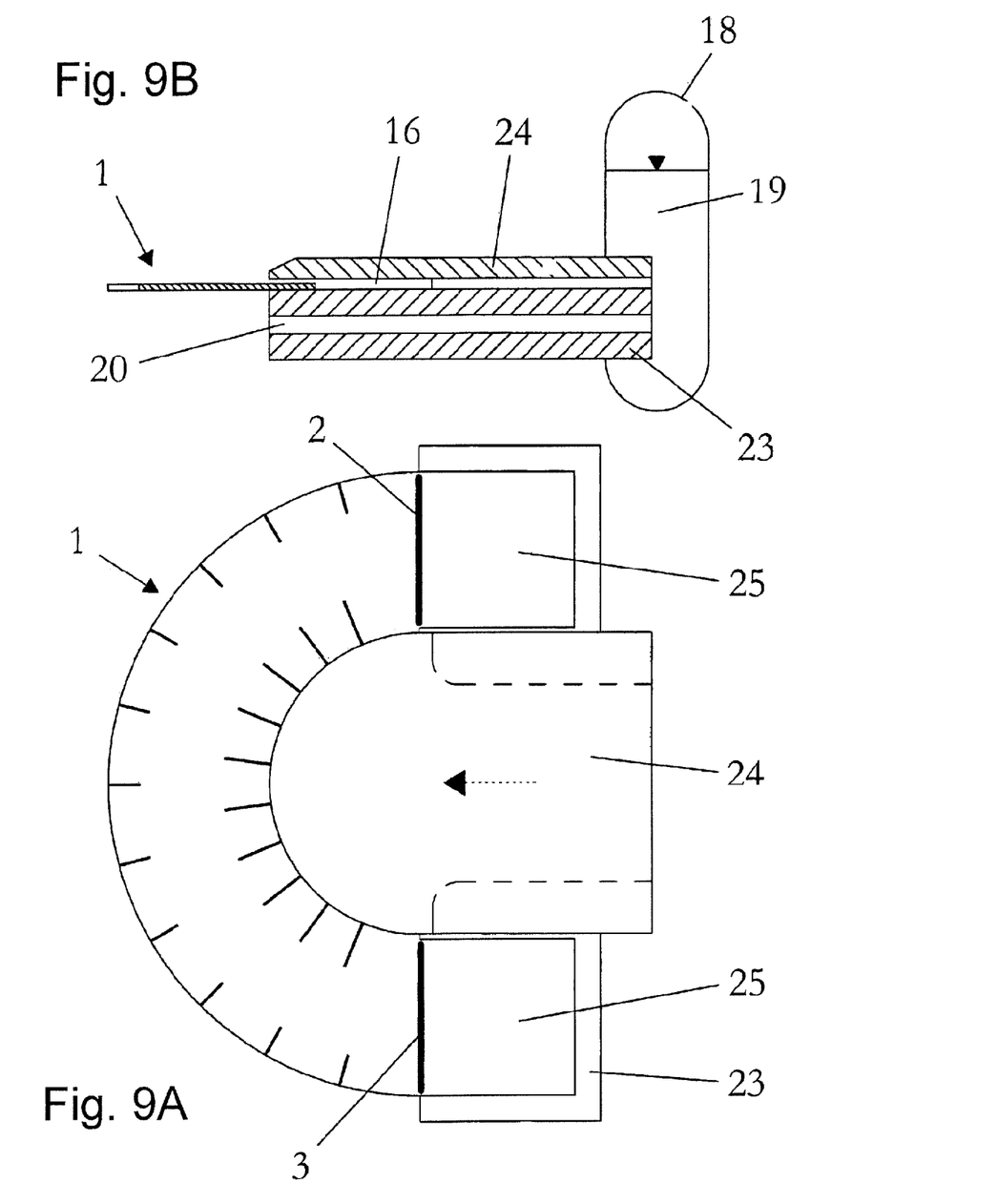
FIG. 9A is a top plan view of an evaporator arrangement with automatic liquid supply.
FIG. 9B is a sectional view of the evaporator arrangement of FIG. 9A.

FIGS. 8, 9A and 9B show a circular evaporator arrangement. The laminar evaporator 1 is again constructed as shown in Table 1 and is again supplied in this example via a capillary gap 16 with the liquid 19 to be evaporated. In contrast to the previous example the filling of the capillary structure here takes place transverse to the lines of flux of the original electric field and the slot-shaped recesses and/or cuts 5 point in the direction of feeding. Specifically, the feeding takes place radially from the inside outwards (suggested in FIG. 8 by arrows) and the cuts 5 are likewise radially aligned. This kind of feeding has the advantage that the capillary current in the wick is not obstructed by the cuts 5. Cuts are intended both at the inside and at the outside periphery. The cuts at the inner periphery form tongues 22, which partly project into the capillary gap 16 and in this way cause the capillary coupling with the liquid 19. The capillary gap 16 is formed by a printed circuit board 23 and a cover plate 24 placed on its surface, in that a corresponding recess, e.g. a milled slot, is formed in the cover plate 24. The capillary gap 16 draws the liquid 19 to be evaporated from a liquid reservoir 18 (represented symbolically in FIG. 9B), and a ventilation hole 20 is also again intended to balance the pressure. Electrical contact with the laminar evaporator 1 is made by two extensions 25, by fastening the latter, preferably on the foil side, by means of a conductive adhesive to the printed circuit board 23. The poles 2, 3 are in each case suggested by a thick line in FIG. 9A.

In selecting the materials for the construction units for forming the capillary gap 16 care should be taken to achieve good wettability of the same with the liquid to be evaporated 19. This condition is valid both for the arrangement in accordance with FIGS. 7A and 7B and for the arrangement in accordance with FIGS. 9A and 9B.

The structure of a laminar evaporator in accordance with the invention shown as an example in Table 1 is based on the fact that several metal fabric layers are sintered onto a metal foil. With evaporators of this design the vapors formed can only exit from the porous structure on the side opposite the metal foil. As an alternative to this design laminar evaporators with the porous structure open on both sides can also be used where it is particularly advantageous if the resistance heating element is formed entirely of the porous structure. Laminar evaporators of this design allow particularly high evaporation rates. Such an evaporator can, for example, consist of an electrically conducting open-pored foam material. Such foam material made of e.g. AISI 316L stainless steel can be obtained from the company Mitsubishi Materials Corporation, www.mmc.co.jp. Here the starting point was a standard foam material with a thickness of 0.5 mm, a pore diameter within the range 50-150 µm and a porosity of about 90%. The material can be reduced by rollers as required to a thickness of, for instance, 100 µm. The consolidated material can subsequently still be sintered if required. The compression naturally also reduces the porosity, which can be increased again, however, if necessary in the course of a subsequent etching treatment. Heat-conducting alloys, in particular from the group of NiCr alloys, e.g. NiCr8020, DIN material No. 2.4869, can be likewise converted to such a foam material. The laminar evaporator can consist of a single foam layer or of several foam layers sintered together. To increase the stability and strength of the laminar evaporator the foam can optionally be sintered onto a thin support layer, for example onto a wire mesh of stainless steel or a heat-conducting alloy. The laminar foam material can be made to any shape by laser cutting. The slot-shaped recesses and/or cuts in accordance with the invention are again preferably made in the foam material by means of an Nd:YAG laser.

In all the foregoing examples shown the slot-shaped recesses and/or cuts proceed from the edges of the laminar evaporator. The invention is, of course, not limited to this arrangement. Rather the slot-shaped recesses and/or cuts can also be disposed spaced apart from the edges. Slots arranged in this way have a double-constricting effect, since in this case both ends of slit restrict the lines of flux of the original electric field.

REFERENCE SYMBOL LIST 1 laminar evaporator
2 first pole
3 second pole
4 lines of flux of the original electric field
5 slot-shaped recess; cut
6 constricted lines of flux
7 edge
8 end of slit
9 zone of high electric field strength
10 zone of low electric field strength
11 zone of highest power density
12 edge zone of lowest power density 13 middle zone of medium power density
14 plate-shaped contact element
15 periphery
16 capillary gap
17 upper section
18 liquid reservoir
19 liquid
20 vent hole
21 main supply channel
22 tongue
23 printed circuit board
24 cover plate
25 extension

The invention claimed is:

1. An evaporator comprising:
an electrical resistance heating element for pulse heating and evaporation of an inhalationally receivable material distributed or distributable on a surface of the electrical resistance heating element by an electric heating current flowing or flowable in a laminar manner with at least two electrical contacts or poles for introducing the electric heating current into the electrical resistance heating element,
wherein the electrical resistance heating element has at least one cut constricting lines of flux of an original electric field forming or formable between the at least two electrical contacts or poles and comprises a porous structure having a porosity of 70% or greater holding or capable of holding the material, the at least one cut being spaced apart from edges of the electrical resistance heating element.

2. The evaporator of claim 1, wherein the electrical resistance heating element consists of an electrically resistant material and the at least one cut penetrates the electrical resistance heating element.

3. The evaporator of claim 2, wherein the electrical resistance heating element is formed entirely by the porous structure.

4. The evaporator of claim 3, wherein the porous structure forms a wick.

5. The evaporator of claim 1, wherein the at least one cut extends essentially in a straight line and is aligned at least approximately at right angles to the lines of flux of the original electric field constricted by the at least one cut.

6. The evaporator of claim 1, wherein the electrical resistance heating element consists of a metallic resistance material.

7. The evaporator of claim 1, wherein the at least one cut comprises a plurality of cuts.

8. The evaporator of claim 7, wherein the plurality of cuts are unevenly closely distributed on the surface of the electrical resistance heating element.

9. An inhaler component comprising at least one evaporator according to claim 1.

10. An inhaler component comprising the evaporator of claim 4 and with a source of liquid, communicating or capable of communicating via capillary action with the wick to supply the wick with the liquid, wherein the wick is supplied with the liquid in a direction of the lines of flux of the original electric field and the at least one cut comprises a plurality of cuts arranged staggered one behind another in a row aligned essentially parallel to the lines of flux.

11. An inhaler component comprising the evaporator of claim 4 and with a source of liquid communicating or capable of communicating via capillary action with the wick to supply the wick with the liquid, wherein the wick is fed transverse to the lines of flux of the original electric field with the liquid and the at least one cut points essentially in a direction of filling.

12. An evaporator comprising:
an electrical resistance heating element for pulse heating and evaporation of an inhalationally receivable material distributed or distributable on a surface of the electrical resistance heating element by an electric heating current flowing or flowable in a laminar manner with at least two electrical contacts or poles for introducing the electric heating current into the electrical resistance heating element,
wherein the electrical resistance heating element has at least one cut constricting lines of flux of an original electric field forming or formable between the at least two electrical contacts or poles,
wherein the electrical resistance heating element consists of an electrically resistant material and the at least one cut penetrates the electrical resistance heating element and is spaced apart from edges of the electrical resistance heating element,
wherein the electrical resistance heating element is formed entirely by a porous structure.

* * * * *